United States Patent [19]

Campbell

[11] Patent Number: 5,362,899
[45] Date of Patent: Nov. 8, 1994

US005362899A

[54] CHIRAL SYNTHESIS OF ALPHA-AMINOPHOSPONIC ACIDS

[75] Inventor: David A. Campbell, Redwood Shores, Calif.

[73] Assignee: Affymax Technologies, N.V., Curacao, Netherlands

[21] Appl. No.: 120,007

[22] Filed: Sep. 9, 1993

[51] Int. Cl.$^5$ ............................................. C07F 9/40
[52] U.S. Cl. ................................... 558/108; 558/122; 558/124; 558/166; 558/170; 558/172; 558/173
[58] Field of Search ................. 558/166, 122, 124, 131

[56] References Cited

PUBLICATIONS

Arbusow, 1964, Pure Applied Chem. 9:307–335.
Michaelis–Arbusow–und Perkow Reaktionen.
Barton et al., 1973, J. C. S. Perkin I, pp. 599–603.
Transformations of penicillin. Part III. A new route to 2,2-Dimethyl-6beta-phenylacetamidopenam-3alpha-ol S-oxide and its esters: o-Nitrobenzoate as a protecting group for alcohols and phenols.
Bauer et al., 1977, Agnew Chem. Int. Ed. Engle. 16(7):477–478.
Phosphoranes as intermediates in the Michaelis-Arbusov reaction.
Corcoran et al., 1990, Tetrahedron Letters 31 (47):6827–6830.
Conversion of alpha–Aminocarboxylic acids to a–aminophosphonic acids.
Denney et al., 1965, The Carboxy–Inversion Reaction 30:3760–3761.
Degradation of acids to alcohols by the carboxy–inversion reaction.
Galynker et al., 1982, Tetrahedron Letters 23 (43): 4461–4464.
A simple method for tosylation with inversion.
Garegg et al., 1980, J. C. S. Perkin I 2866–2869.
Novel reagent system for converting a hydroxy-group into an iodo-group in carbohydrates with inversion of configuration. Part 2.
Gillard et al., 1981, Tetrahedron Letters 22:513–516.
Trimethysilyl bromide as a mild, stereoselective anomeric brominatiry ajent.
Bryant et al., 1979, J. Org. Chem. 44 (21):3733–3734.
Acyclic nucleoside analogues: Synthesis of open–ring riboside or deoxyriboside analogues lacking C(3) or the C(3)–C(4) bond.
Kochi et al., 1965, J. American Chem. Soc. 87(11):2500–2502.
A new method for halodecarboxylation of acids using lead(IV) acetate.
Jung et al, 1977, J. Org. Chem. 42(23):3761–3764.
Quantitative dealkylation of alkyl esthers via treatment with trimethylsilyliodide. A new method for ether hydrolysis.
Jung et al., 1977, J. American Chem. Soc. 968–969.
Quantitative dealkylation of alkyl esters via treatment with trimethylsily iodide. A new method for ester hydrolysis.
Kopsolapoff., 1951, Organic Reactions 6: 276–279.

(List continued on next page.)

Primary Examiner—Patricia L. Morris
Assistant Examiner—Michael G. Ambrose
Attorney, Agent, or Firm—Kevin R. Kaster; Vern Norviel; Lauren L. Stevens

[57] ABSTRACT

A stereospecific method of preparing alpha-aminophosphonic acids and derivatives thereof is provided. A protected amino acid is converted to a acyl aroyl or diacyl peroxide which spontaneously rearranges to form an alpha-amino ester. This rearrangement occurs stereospecifically with retention of configuration. The ester is subsequently converted to an appropriate leaving group and displaced with a phosphite yielding a chiral alpha-aminophosphonic acid or derivative.

Alpha-aminophosphonic acids are useful for the synthesis of peptide analogs that possess a phosphonate linkage in the place of an amide linkage. This substitution can impart protease resistance in therapeutic peptides thereby increasing the serum half-life.

16 Claims, 1 Drawing Sheet

PUBLICATIONS

Alkylation of the phosphorus atom in phosphorus esters.
Redmore., 1971, Chemical Review 9:307–337.
Heterocyclic systems bearing phosphorus substituents synthesis and chemistry.
Seebach et al., 1989, Helvetica Chimica Acta 72:401–425.
50. Elektrochemische decarboxylierung von L--threonin-und oligopeptid-derivaten unter bildung von N-acyl-N,O-acatalen: Phosphonat-C-Terminus.
Shiozaki, Aug. 1990, Synthesis 691–693.
Scope and limitations of oxidate decarboxylation of alpha-(acylamino) acids by peroxy acids: Conversion of a 2-azetidinone-4-carboxylic acid to a carbapenem.
Shiozaki., 1989, Bull. Chem. Soc. 62:3950–3958.
Synthesis of 2-amino-2-deoxy-alpha-d-altrofuranoside derivatives from 2,3-O-Isopropylidene-d--glyceraldehyde via bicyclic beta-lactam intermediates.
Sheldon and Kochi, 1972, Organic Reactions 19:279–421.
Chapter 4: Oxidative Decarboxylation of acids by lead tetraacetate.

CHIRAL SYNTHESIS OF ALPHA-AMINOPHOSPONIC ACIDS

CROSS-REFERENCE

This application is related to copending U.S. patent application Ser. No. 08/119,700 (Attorney Docket No. 11509-59-2), which is a continuation-in-part of copending U.S. patent application Ser. No. 08/081,577, filed Jun. 21, 1993, which is also a continuation-in-part of copending U.S. patent application Ser. No. 07/943,805, filed Sep. 11, 1992. These applications are expressly incorporated herein by reference for all purposes.

BACKGROUND OF THE INVENTION

The present invention relates to alpha-aminophosphonic acids, and derivatives thereof, and methods of preparing them. More specifically, the invention pertains to synthetic routes in which the chirality of an amino acid starting material is preserved during a series of reactions to produce an alpha-aminophosphonic acid or alpha-aminophosphonate.

Aminophosphonic acids and aminophosphonates are derivatives of amino acids in which the amino acid carboxyl group has been replaced with a phosphonic acid or phosphonate moiety. In alpha-aminophosphonic acids and phosphonates, the alpha-carbon atom is often a chiral center, bound to a phosphonate moiety, an amine moiety, and one or more amino acid side chains. The structure can be represented as follows:

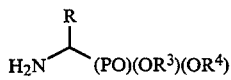

in the displayed structure, R represents any amino acid side chain and $R^3$ and $R^4$ represent hydrogen (in the case of a phosphonic acid) or a group such as alkyl or aryl (in the case of a phosphonate ester).

Alpha-aminophosphonates have various uses; many of which involve synthesis of peptide analogs (peptidylphosphonates) that possess a phosphonate linkage in the place of at least one amide link in the peptide main chain. Because the phosphonate linkage exists as a charged moiety in the peptide backbone, it increases the water solubility of the peptide. Further, the phosphonate linkage can impart protease resistance and therefore increase the serum half-life of many therapeutic peptides.

In addition, substitution of the phosphonate linkage for the amide linkage allows for the introduction of additional functionalities into regions of space inaccessible in naturally occurring peptides. Specifically, amide linkages are planar, so peptides have a flat configuration in the area of the carboxylic acid linkage. Phosphonate linkages, however, are tetrahedral. This tetrahedral geometry allows for the presence of substituents in the areas above and below the plane of the carboxylic acid linkage of a peptide. Moreover, the tetrahedral configuration of the phosphonate linkage can be exploited to optimize enzyme-inhibitor or ligand-receptor binding. See Bartlett and Marlowe (1983) *Biochemistry* 22:4618-24.

Literature examples of specific uses of peptidylphosphonates are numerous; these compounds are recognized as effective transition-state analog inhibitors for a variety of enzymes, including a number of proteases and esterases (see, e.g., Morgan et al., (1991) *J. Am. Chem. Soc.* 113:297 and Bartlett et al.,(1990) *J. Org. Chem.* 55:6268). Peptidylphosphonate esters have been used as nonhydrolyzable analogs of phosphates to inhibit dinucleoside triphosphate hydrolase (see, e.g., Blackburn et al., (1987) *Nucl. Acids Res.* 15:6991), phosphatidyltransferase (see, e.g., Vargas et al. (1984) *Biochim. Biophys. Acta* 796:123), and squalene synthetase (see, e.g, Biller et al. (1988) *J. Med. Chem.* 31:1869). The most potent noncovalent enzyme inhibitor known is a phosphonyltripeptide inhibitor of carboxypeptidase A, which binds with 11 femptomolar (fM) $K_d$ (see Kaplan et al. (1991) *Biochem.* 30:8165-8170). In addition, phosphonate esters have been used as haptens for the production of catalytic: antibodies possessing esterase activity (see, e.g., Jacobs et al. (1987) *J. Am. Chem. Soc.* 109:2174; Tramontano et al. (1986) *Science* 234:1566; and Pollack et al. (1986) Science 234:1570; see also, U.S. patent application Ser. No. 07/858,298, filed Mar. 26, 1992). Some peptidylphosphonate analogs are commercially available. For instance, the drugs Monopril and Fosinopril are available from Bristol Myers, Squibb (Evansville, Ind.).

Recently, innovative combinatorial strategies for synthesizing large numbers of polymeric compounds on solid supports have been developed. One such method, referred to as VLSIPS TM ("Very Large Scale Immobilized Polymer Synthesis"), is described in U.S. patent application Ser. No. 07/805,727, filed Dec. 6, 1991, which is a continuation-in-part of Ser. No. 07/624,120, filed Dec. 6, 1990, which is a continuation-in-part of U.S. Pat. No. 5,143,854, which is a continuation-in-part of Ser. No. 07/362,901, filed Jun. 7, 1989, and now abandoned. Such techniques are also described in PCT publication No. 92/10092. Related combinatorial techniques for synthesizing polymers on solid supports are discussed in U.S. patent application Ser. No. 07/946,239 filed Sep. 16, 1992 which is a continuation-in-part of Ser. No. 07/762,522 filed Sep. 18, 1991 and U.S. patent application Ser. No. 07/980,523 filed Nov. 20, 1992 which is a continuation-in-part of Ser. No. 07/796,243 filed Nov. 22, 1991. Briefly, a combinatorial synthesis strategy is an ordered strategy for parallel synthesis of diverse polymer sequences by sequential addition of reagents to a solid support. These techniques can be extended to produce immobilized peptidylphosphonates in large arrays of polymers. For example, U.S. patent application Ser. No. 07/943,805 discusses the use of monoesters of alpha-aminophosphonic acids to synthesize peptidylphosphonates on solid supports. Each of the references mentioned in this paragraph are incorporated herein by reference for all purposes.

Methods of preparing amino phosphonates are known. For example, they can be prepared by the addition of phosphite to imines. In addition, they may be produced from amino acids by the procedure of Corcoran et al. (1990) *Tetr. Lett.* 31:6827-6830. The Corcoran et al. reference describes the oxidative decarboxylation of N-protected amino acids with lead tetraacetate to form the corresponding O-acetyl-N,O-acetal. Subsequent treatment with a phosphite yields the corresponding phosphonate or phosphonic acid. Further, compounds having the following structure where Z is either iodo, bromo, or chloro, can be prepared through the treatment of an N-protected amino acid with lead tetraacetate and the appropriate halide ions.

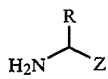

This general procedure is reported in Kochi (1965) *J. Am. Chem. Soc.* 87:2500, and a review of this reaction can be found in Sheldon and Kochi (1972) *Org. React.* 19:279–421. Alternatively, the above compound, where Z is either iodo, bromo, or chloro, can be prepared from an N-protected amino acid using the procedures outlined in March, 1985, *Advanced Organic Chemistry* 3rd Ed., (John Wiley & Sons, New York), pp. 654–655.

The corresponding alpha-aminophosphonate can be prepared through the reaction of the above compound, where Z is acetoxy or halo, with a suitable phosphite such as trimethylphosphite. See Corcoran, supra; see also, Seebach et al. (1989) *Helv. Chim. Acta* 72:401. A review of this general reaction can be found in Arbuzow (1964) *Pure Appl. Chem.* 9:307. For example, when Z is acetoxy, the above acyl compound may be treated with trimethylphosphite in the presence of titanium tetrachloride to produce the trimethyl ester of an alpha-aminophosphonic acid.

However, the above procedure will not produce a stereospecific alpha-amino phosphonic acid. As the treatment of the acetoxy compound with $TiCl_4$ generates an iminium ion which destroys any chirality that may have been present in the starting materials, the decarboxylation step (as employed in the procedure of Corcoran et al.) does not result in any significant enantiomeric excess. Moreover, even if racemic aminophosphonic acids are acceptable, the harsh reaction conditions employed in the above synthesis can often limit applicability to simple amino acids.

Various other syntheses of aminophosphonic acids have been reported. For example, the side chain R group can be attached to a suitably protected aminomethylphosphonic acid. However, the available methods are limited in that either they produce racemic alpha-aminophosphonic acids and/or they work with only a few amino acids.

Shiozaki (1990) *Synthesis* 691–693, which is incorporated herein by reference for all purposes, describes a synthetic route for decarboxylating alpha-amino acids with retention of configuration. In this method, amine protected alpha-amino acids are coupled to 3-chloroperoxybenzoic acid or peroxybenzoic acid in the presence of 1,3-dicyclohexylcarbodiimide (DCC) to give the corresponding acyl aroyl peroxide shown below.

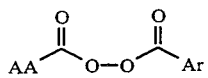

AA is an amino acid residue (i.e. protected amine group, alpha carbon, and side chain) and Ar is an aryl group from the peracid (peroxybenzoic acid or 3-chloroperoxybenzoic acid in Shiozaki). For some alpha-amino acids, most notably those in which the protected alpha-amine group contains no hydrogen atoms, the acyl aroyl peroxide undergoes oxidative decarboxylation to give an ester (shown below) with retention of configuration (see Shiozaki, supra).

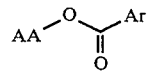

The Shiozaki article shows how this reaction might be used in carbapenem synthesis. The mechanism of the rearrangement to the acetoxy compound is described in Denney and Sherman (1965) *J. Org. Chem.* 30: 3760.

The method of Shiozaki might be a potentially useful decarboxylation step in a synthetic scheme for preparing alpha-aminophosphonic acids with retention of configuration. However, a suitable synthesis must include other steps that ensure that the configuration is preserved throughout the entire synthesis. Thus, for example, the use of $TiCl_4$ with a phosphite as employed in the method of Corcoran et al. would be unacceptable. It is apparent that there remains a need for a mild stereospecific method of preparing alpha-aminophosphonates from corresponding amino acids.

SUMMARY OF THE INVENTION

The present invention provides a stereospecific method of preparing aminophosphonic acids and derivatives thereof from the corresponding amino acids. An amine-protected amino acid is first converted to its acyl aroyl or diacyl peroxide via suitable coupling conditions such as carbodimide coupling. The resulting peroxide spontaneously rearranges via a Curtius-type rearrangement to form an amino ester. This rearrangement occurs stereospecifically with retention of configuration. The ester group is subsequently converted to an appropriate leaving group which is then displaced with a phosphite to yield a chiral alpha-aminophosphonic acid or derivative thereof with a net inversion of configuration.

In a preferred embodiment, the method of the present invention includes the following steps:

(a) treating a compound of Formula I:

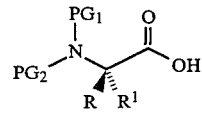

in which $PG_1$ and $PG_2$ are protecting groups, R and $R^1$ are independently selected from the group consisting of hydrogen, alkyl, aryl, substituted alkyl, substituted aryl, heteroaryl, alkylaryl, and aminoalkyl, provided that R is not the same as $R^1$ and provided that either R or $R^1$ is hydrogen, with a peracid having the structure $R^2(CO)OOH$, in which $R^2$ is alkyl or aryl, to yield an ester of Formula III:

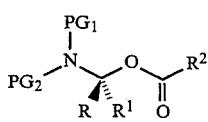

in which $PG_1$, $PG_2$, R, $R^1$, and $R^2$ are defined as above;

(b) stereoselectively replacing the $R^2COO—$ group from the ester of Formula III with a leaving group X with either retention or inversion of configuration, wherein the leaving group X is a halide or a sulfonate, to yield a compound of Formula IV or VI, respectively:

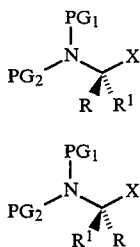

(IV)

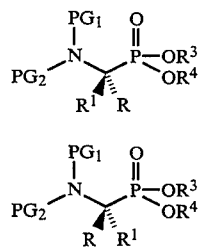

(VI)

in which PG₁, PG₂, R, R¹, and X are defined as above; and (c) treating the compound of Formula IV or VI, in which PG₁, PG₂, R, R¹, and X are defined as above, with a phosphite having the structure P(OR³)((OR⁴)(OR⁵), in which R³, R⁴, and R⁵ are independently lower alkyl or aryl, to yield a compound of Formula V or VII, respectively:

(V)

(VII)

The alpha-amino acid starting material can be a natural (genetically coded) or unnatural amino acid. In preferred embodiments, the amine group of the amino acid is protected so that amine nitrogen contains no hydrogen atoms. Phthalimide protected amino acids are particularly preferred. The peracid utilized in step (a) is preferably an aryl peracid such as peroxybenzoic acid or 3-chloroperoxybenzoic acid. A suitable acyl peracid is peracetic acid. The leaving group introduced in step (b) is preferably a halide, such as bromide or halide, or a sulfonate group, such as the p-toluenesulfonate group. Halide leaving groups can be introduced by converting the alkyl or aryl carboxy group directly to a halide with halotrimethylsilane ((CH₃)₃SiX, where X=Br or I). Alternatively, the ester group can be first hydrolyzed to an alcohol which is subsequently converted to a halide or other leaving group.

Preferably, the steps of converting the alkyl or aryl carboxy group to an appropriate leaving group and reacting the resulting compound with a phosphite are performed under conditions that retain the chirality of the carbon atom adjacent the leaving group (i.e. the alpha-carbon in the amino acid starting material). This approach takes advantage of the stereospecificity of the Curtius-type rearrangement to permit chiral synthesis of alpha-aminophosphonic acids or phosphonates, and particularly peptidyl phosphonates.

A further understanding of the invention may be had by reference to the following detailed disclosure and the associated drawing.

DESCRIPTION OF THE SPECIFIC EMBODIMENTS

I. Terminology

Figure 1:
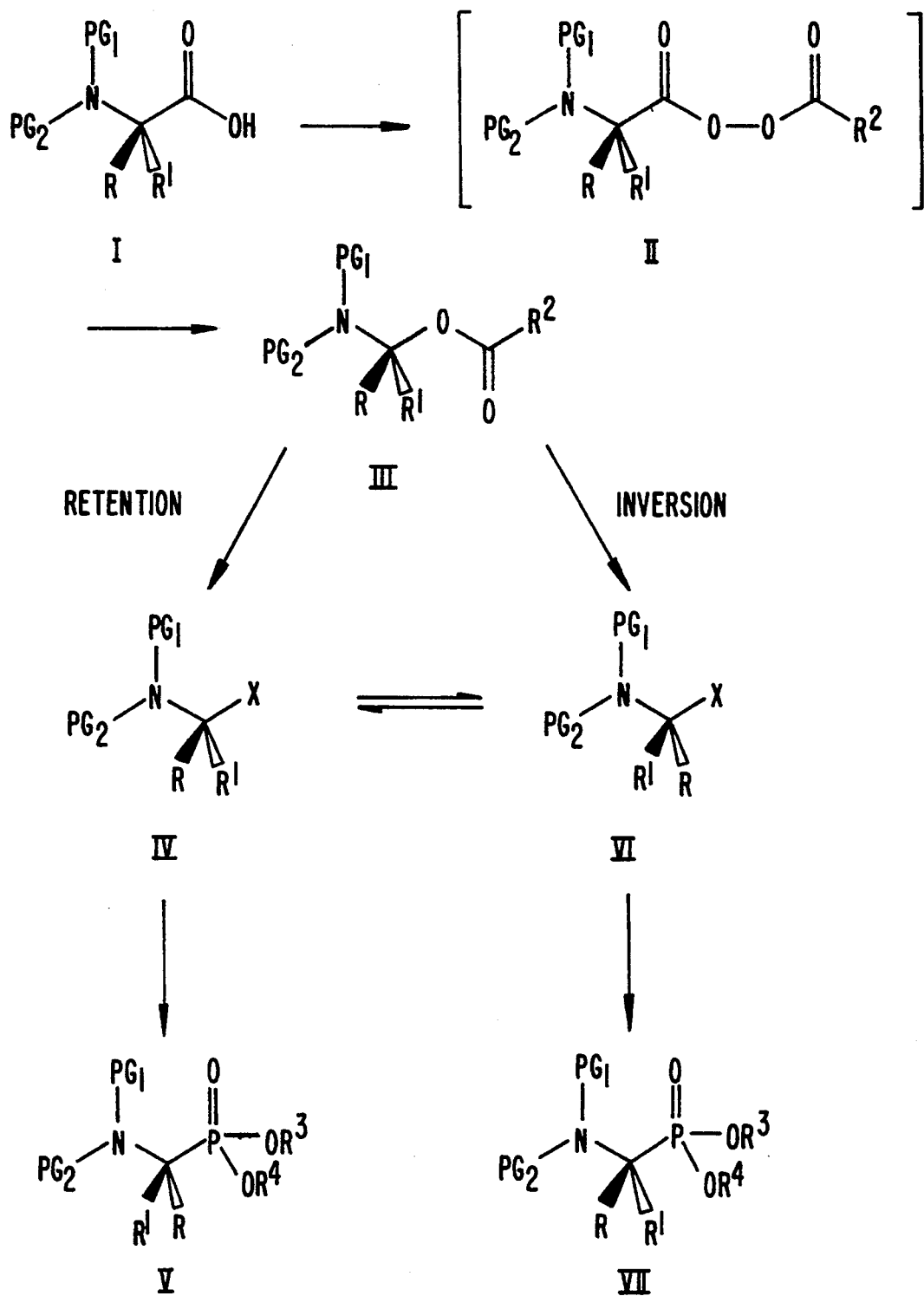
FIG. 1 shows a reaction scheme for stereospecific synthesis of alpha-aminophosphonates according to this invention.

For purposes of clarity and a complete understanding of the invention, the following terms are defined.

"Acyl" refers to the class of groups represented by R—C(O)—, where R is an alkyl group.

"Alkyl" refers to a cyclic, branched, or straight chain chemical group containing only carbon and hydrogen, such as methyl, heptyl, —(CH₂)₂—, and adamantyl. Alkyl groups can either be unsubstituted or substituted with one or more substituents, e.g., halogen, alkoxy, acyloxy, amino, hydroxyl, mercapto, carboxy, benzyloxy, phenyl, benzyl, or other functionality which may be suitably blocked, if necessary for purposes of the invention, with a protecting group. Typically, alkyl groups will comprise 1 to 12 carbon atoms, preferably 1 to 10, and more preferably 1 to 8 carbon atoms.

"Alkyl silyl" refers to the group —SiRR'R" where R, R', and R" are independently lower alkyl.

"Aprotic, polar solvent" refers to organic solvents which may be either water insoluble, such as halogenated hydrocarbons (e.g., methylene chloride, chloroform, and carbon tetrachloride) or water miscible, such as tetrahydrofuran, dimethoxyethane, N,N-dimethylformamide, and dimethylsulfoxide.

"Aroyl" refers to the class of compounds represented by Ar—C(O)—, where Ar is an aryl group.

"Aryl" or "Ar" refers to an aromatic carbocyclic group having a single ring (e.g., phenyl) or multiple condensed rings (e.g., naphthyl or anthryl), which can optionally be unsubstituted or substituted with amino, hydroxyl, lower alkyl, alkoxy, chloro, halo, mercapto, and other substituents. Preferred aryl groups include phenyl, 1-naphthyl, and 2-naphthyl.

"Arylalkyl" refers to the groups R—Ar and R—HetAr, where Ar is an aryl group, HetAr is a heteroaryl group, and R is straight-chain or branched-chain aliphatic group. Examples of arylalkyl groups include benzyl and furfuryl.

"Heteroaryl" or "HetAr" refers to a monovalent unsaturated aromatic carbocyclic group having a single ring (e.g., pyridyl or furyl) or multiple condensed rings (e.g., indolizinyl or benzothienyl) and having at least one hetero atom, such as N, O, or S, within the ring, which can optionally be unsubstituted or substituted with amino, hydroxyl, alkyl, alkoxy, halo, mercapto, and other substituents.

"Leaving group" refers to that part of a substrate molecule which is cleaved in a chemical reaction. The ability of a substance to act as a leaving group is usually inverse to its basicity, with the best leaving groups being the weakest bases. Examples of leaving groups include, but are not limited to, halides, such as bromide and iodide, and sulfonates, such as p-toluenesulfonates (tosylates (—OTs), see, e.g., Fieser and Fieser, *Reagents for Organic Synthesis*, Vol. 1, Wiley, New York (1967), p. 1179), p-bromobenzenesulfonates (brosylates, see, e.g., Awad et al. (1986) *Bull. Chem. Soc. Jpn.* 59:1587), p-nitrobenzenesulfonates (nosylates), methanesulfonates (mesylates, see, e.g., Furst and Koller (1947) *Helv. Chim. Acta* 30:1454), trifluoromethanesulfonates (triflates, see, e.g., Stang et al. (1982) *Synthesis* 85–126 and Howels and McCown (1977) *Chem, Rev.* 77:69–92); nonafluorobutanesulfonates (nonaflates, see, e.g., Stang et al. (1982) *Synthesis* 85–126 and Howels and McCown (1977) *Chem. Rev.* 77:69–92), 2,2,2-trifluoroethanesulfonates (tresylates, see, e.g., Crossland et al., (1971) *J. Am. Chem. Soc.* 93:4217).

"Lower alkyl" refers to an alkyl group of one to six carbon atoms. Lower alkyl groups include those exemplified by methyl, ethyl, n-propyl, i-propyl, n-butyl, t-butyl, i-butyl (2-methylpropyl), cyclopropylmethyl, i-amyl, n-amyl, and hexyl. Preferred lower alkyls are methyl and ethyl. If more than one alkyl group is present in a given molecule, then each may be independently selected from "lower alkyl" unless otherwise stated.

"Peracid" refers to a compound having the functionality —(CO)OOH.

"Phosphonate ester," "alkylphosphonate ester," "alkylphosphonic acid ester," or "phosphonic acid ester" refers to the group (RPO)(OR')(OR") where R, R' and R" are independently selected from the group consisting of hydrogen, alkyl, substituted alkyl, aryl, substituted aryl, arylalkyl, heteroaryl, alkyl silyl (such as trimethylsilyl), and the like, provided both R' and R" are not hydrogen, in which case the group is a phosphonic acid.

"Phosphonic acid" or "alkylphosphonic acid" refers to the class of compounds denoted by $(RPO)(OH)_2$.

"Phosphite" refers to compounds having the structure $(RO)_3P$ where R is alkyl or aryl.

"Protecting group" refers to a chemical group that exhibits the following characteristics: (1) reacts selectively with the desired functionality in good yield to give a protected substrate that is stable to the projected reactions for which protection is desired; (2) is selectively removable from the protected substrate to yield the desired functionality; and (3) is removable in good yield by reagents compatible with the other functional group(s) generated in such projected reactions.

"Stereospecific reaction" refers to a reaction in which bonds are broken and made at a single asymmetric atom (usually, but not necessarily carbon), and which lead largely to a single stereoisomer. If the configuration of the asymmetric carbon is altered in the process, the reaction is said to involve an inversion of configuration. If the configuration of the asymmetric carbon remains the same, the transformation occurs with retention of configuration.

"Sulfonate" refers to a salt or ester of a sulphonic acid ($-SO_2OH$) and thus, refers to the linkage $-SO_2O-$.

II. Compounds of Formula I

An exemplary synthesis according to this invention is shown in FIG. 1. The alpha-aminophosphonates of this invention, i.e., the compounds of Formulas V and VII, are produced from alpha-amino acid starting materials, compounds of Formula I. Typically, the alpha-carbon atom of an alpha-amino acid is bonded to an amine group, a carboxyl group, a hydrogen atom, and a distinctive group referred to as a "side chain." The hydrogen atom may also be replaced with a group such as alkyl, substituted alkyl, aryl, substituted aryl, heteroaryl, and other groups. The side chains of naturally occurring amino acids are well known in the art and include, for example, hydrogen (as in glycine), alkyl (as in alanine, valine, leucine, isoleucine, proline), substituted alkyl (as in serine, cysteine, aspartic acid, asparagine, arginine, glutamine, glutamic acid, threonine, and lysine), arylalkyl (as in phenylalanine, histidine, and tryptophan), substituted arylalkyl (as in tyrosine and thyroxine), and heteroaryl (as in histidine). See, e.g., Harper et al., 1977, *Review of Physiological Chemistry*, 16th Ed., Lange Medical Publications, pp. 21–24.

Thus, the "R" and "R" groups, for example in the compounds of Formula I or II, represent either hydrogen or the side chain of the amino acid starting material. The side chains of naturally occurring amino acids are well known in the art and include, for example, hydrogen (as in glycine), alkyl (as in alanine (methyl), valine (isopropyl), leucine (sec-butyl), isoleucine (iso-butyl), and proline ($-(CH_2)_3-$)), substituted alkyl (as in serine (hydroxymethyl), cysteine (thiomethyl), aspartic acid (carboxymethyl), asparagine, arginine, glutamine, glutamic acid, and lysine), arylalkyl (as in phenylalanine, histidine, and tryptophan), substituted arylalkyl (as in tyrosine and thyroxine), and heteroaryl (as in histidine). See, e.g., Harper et al. (1977) *Review of Physiological Chemistry*, 16th Ed., Lange Medical Publications, pp. 21–24. Additional specific examples of side chains found in naturally occurring amino acids include 1-hydroxyethyl, thiomethyl, 2-methylthioethyl, carboxymethyl, carbamoylmethyl, carboxyethyl, carbamoylethyl, 3-guanidinopropyl, 4-aminobutyl, 4-amino-3-hydroxybutyl, 1H-imaidaxoylmethyl, benzyl, p-hydroxybenzyl, 3-indolylmethyl, $-(CH_2)_3-$, $-CH_2CHOHCH_2-$, 2-thioethyl, 2-hydroxyethyl, 3-aminopropyl, 3-ureidopropyl, 3,4-dihydroxybenzyl, and the like.

In addition to naturally occurring side chains, the amino acids used in the present invention may possess synthetic side chains. A "synthetic side chain" is any side chain not found in a naturally occurring amino acid. For example, a synthetic side chain can be an isostere of the side chain of a naturally occurring amino acid. Naturally occurring and synthetic side chains may contain reactive functionalities, such as hydroxyl, mercapto, and carboxy groups. One skilled in the art will appreciate that these groups may have to be protected to carry out the desired reaction scheme.

As stated above, the hydrogen at the alpha-carbon can also be replaced with other groups; those of skill in the art recognize the medicinal importance of alpha-methyl amino acids and other alpha, alpha-disubstituted amino acids. It should be recognized, however, that the alpha hydrogen of alpha-amino acid starting materials described herein preferably is not replaced with other groups since stereospecific nucleophilic attack on tertiary centers can be difficult to accomplish. If an alpha, alpha disubstituted aminophosphonic acid is desired, preferably, the second alpha substituent is introduced after the formation of the phosphonate group. Thus, in a preferred embodiment, either R or $R^1$ will be hydrogen.

The amine group of the amino acid of Formula I preferably is protected. One skilled in the art will appreciate that any one of a variety of terminal amino protecting groups may be used. Examples of terminal amino protecting groups may be found in Greene et al., 1991, *Protective Groups in Organic Synthesis*, 2nd Ed. (John Wiley & Sons, Inc., New York), which is incorporated herein by reference for all purposes, and include carbamates, bis-carbamates, amides, bis-amides, N-alkyl groups, N-aryl groups, etc. As noted above, the protecting group(s) should replace all available hydrogen atoms on the amine nitrogen so that the resulting protected amine groups has no hydrogen atoms. A particularly preferred amine protecting group is phthalic acid which forms a phthalimide with the alpha-amine group. When the amine has a free proton, any good leaving group attached will spontaneously eliminate to produce an iminium ion. Generation of the iminium ion should be avoided because it will generally racemize the desired product. Use of the phthalimide group eliminates the amine proton and in addition is sufficiently electron withdrawing to prevent the nitrogen's lone pair electrons from eliminating the leaving group.

III. Preparation of Compounds Of Formula III

Standard condensing conditions are used to couple the peracid with the protected alpha-amino acid of Formula I to form the diacyl or acyl aroyl peroxide of Formula II. Suitable condensing conditions include conventional carbodiimide coupling. For example, a solution of the alpha-amino acid in a polar aprotic solvent, such as ethyl acetate, chloroform, N,N-dimethylformamide, or dichloromethane, is stirred with a peracid, typically between about 1 and 5 equivalents, preferably between about 1 and 3 equivalents, and more preferably between about 1 and 1.5 equivalents, and then 1,3-dicyclohexylcarbodiimide (DCC), typically between about 1 and 5 equivalents, preferably between about 1 and 3 equivalents, and more preferably between about I and 1.5 equivalents. The reaction is conducted at between 0° and 25° C. for approximately 5-60 minutes. After evolution of carbon dioxide has ceased, the mixture is filtered and chromatographed.

Various commercially available aryl and alkyl peracids may be used. Preferred peracids include peroxybenzoic acid, 3-chloroperoxybenzoic acid, 4-nitroperoxybenzoic acid, and peracetic acid. The "$R^2$" group of compounds of Formulas II and III is derived from the peracid and typically will comprise an alkyl or aryl group.

Alternatively, the diacyl or acyl aroyl peroxides of Formula II might be prepared by direct coupling of a peracid with an activated derivative of the amino acid starting materials. The following compounds might be employed: amino acid halides, halo-formates, mixed anhydrides, imidazolyl formates, etc. For example, an alpha-amino acyl chloride could be reacted with a peracid in the presence of a suitable solvent such as chloroform or hexane to give the desired peroxide. Acyl chlorides of amino acids may be prepared from the amino acid by treatment with thionyl chloride, phosphorus trichloride, or phosphorus pentachloride as is known to those of skill in the art. The acyl chloride may be reacted with the peracid by, for example, combining them in a solution or suspension and adding pyridine dropwise with cooling and stirring.

The diacyl or acyl aroyl peroxide of Formula II will spontaneously decarboxylate to form an ester of Formula III via a Curtius-type rearrangement. In some instances, heating (e.g. under reflux) may be required to force the reaction to proceed at an appreciable rate, especially if the alpha-carbon bears two hydrogens, as in, for example, a beta-amino acid starting material. Decarboxylation can be allowed to proceed until an infrared spectra of the mixture indicates that the peroxide has decomposed. Like the Curtius and Hofmann rearrangements of acyl azides and amides, this rearrangement occurs stereospecifically, preserving the configuration about the chiral alpha-carbon of the amino acid.

IV. Preparation of Compounds of Formulas IV and VI

Next, the alkyl or aryl carboxy group (—OC(O)$R^2$) of the ester of Formula III is replaced by a leaving group (X) that is susceptible to replacement via nucleophilic substitution. Known leaving groups include anions of various strong acids. Preferred leaving groups for this invention can be coupled to the alpha-amino compound stereospecifically with retention or inversion of configuration. For example, sulfonates, such as p-toluenesulfonates (tosylates), p-bromobenzenesulfonates (brosylates), p-nitrobenzenesulfonates (nosylates), methanesulfonates (mesylates), trifluoromethanesulfonates (triflates); nonafluorobutanesulfonates (nonaflates), 2,2,2-trifluoroethanesulfonates (tresylates) and halides, such as bromide and iodide, are suitable leaving groups.

Various methods may be employed to replace the alkyl or aryl carboxy group of the ester of Formula III with a leaving group. In one preferred embodiment, the ester of Formula III is first hydrolyzed to yield an alcohol of Formula III where X is hydroxyl. The hydrolysis can be carried out under acidic or basic conditions as is known in the art. For example, the ester of Formula III can be converted to the corresponding alpha-amino alcohol (i.e., a compound of Formula IV where X is —OH) by saponification with ammonium hydroxide in aqueous methanol or with methanolic potassium hydroxide. The hydroxyl group can then be replaced with an appropriate leaving group with retention of configuration to give the compound of Formula IV where X is a leaving group, such as halide or sulfonate. Alternatively, the leaving group can be introduced with inversion of configuration to produce the compound of Formula VI where X is a leaving group, such as halide or sulfonate.

In a preferred embodiment, the leaving group will comprise a sulfonate, and more preferably, a tosylate. The tosylate (i.e., a compound of Formula IV where X is —OTs) can be prepared by treating the alcohol of Formula IV where X is —OH with p-toluenesulfonyl chloride in pyridine or aqueous base. This method for the preparation of the sulfonate will retain the stereochemistry of the starting material. Alternatively, the tosylate of Formula VI can be prepared by reacting the alcohol with (TsO)$_2$Zn, in the presence of diethylazodicarboxylate and triphenylphosphine, according to the procedure set forth in *Tetrahedron Lett.* 23:4461 (1982). This reaction proceeds with inversion of stereochemistry.

According to another preferred embodiment, the leaving group will be a halide, such as bromide or iodide. The halide of Formula VI where X is —Br or —I can be prepared from the amino-alcohol by treating the amino-alcohol of Formula IV where X is —OH, with bromine or iodine, respectively, triphenylphosphine, and imidazole, according to the procedure set form in *JCS Perkin I,* 2866 (1980). This reaction proceeds with inversion of stereochemistry.

Compounds of Formula VI where X is —Br or —I also can be prepared directly from compounds of Formula IV where the leaving group is —OTs, by treatment with a source of nucleophilic halide ion, such as an alkali metal salt of the halide ion, for example, sodium or lithium bromide or sodium or lithium iodide, in a polar, aprotic solvent, such as FIMPA. This reaction sequence will result in net inversion of the stereochemistry of the starting material (i.e., preparation of the sulfonate proceeds with retention, while preparation of the halide proceeds by a SN$_2$ route and inversion of stereochemistry.

Alternatively, compounds of Formula IV where X is —Br or —I can be prepared directly from compounds of Formula III by treatment with bromotrimethylsilane or iodotrimethylsilane, respectively. This reaction, in contrast to the one discussed above for preparing the sulfonate, proceeds with retention of stereochemistry. See, e.g., *Tetrahedron Lett.* 22:513 (1981).

V. Preparation of Compounds of Formulas V and VII

Finally, the leaving group is displaced by a desired phosphite via nucleophilic substitution to yield a chiral alpha-aminophosphonates of Formulas V or VII. See, e.g., Redmore (1971) *Chem. Rex-*, 9:307 and Kosolapoff (1951) *Organic Reactions* 6:276 and Bauer and Haegele (1977) *Angew. Chem. Int. Ed.* 16:477, each of which is incorporated herein by reference. This reaction occurs with inversion of configuration. Suitable phosphites may have the formula $P(OR)_3$, $P(OR)_2(OTMS)$, $P(OR)(OTMS)_2$, $P(OTMS)_3$, etc., where TMS represents trimethylsilyl or other alkyl silyl groups. The reaction conditions should be chosen such that as much chirality as possible is retained. Thus, for example, reaction conditions that favor formation of an iminium ion (e.g. $TiCl_4$ mediated chemistry) should be avoided. See, e.g., Corcoran et al. (1990) *Tetrahedron Lett.* 31:6827:6830, Seebach et al. (1989) *Helv. Chim. Acta* 72:401, and Arbuzov (1964) *Pure Appl. Chem.* 9:307–335.

In the preceding synthesis, the chirality of the original alpha-amino acid starting material is retained throughout the reaction sequence to produce a chiral alpha-aminophosphonate product. Thus, the reaction sequence described herein can be characterized as having a high percent asymmetric synthesis or percent enantiomeric excess where these terms serve as a measure of the extent to which one enantiomer is produced in excess over the other. (For example, a reaction sequence that produces 59% of one isomer and 41% of another isomer would have a percent asymmetric synthesis or percent enantiomeric excess of 59−41%=18%). Typically, the reaction sequence described herein will exhibit at least about a 50% percent enantiomeric excess overall; preferably, at least about a 60% percent enantiomeric excess; more preferably, at least about a 70% percent enantiomteric excess; and even more preferably, at least about an 80% percent enantiomeric excess, where a perfectly stereospecific reaction sequence would have a 100% percent enantiomeric excess. See, e.g., Morrison and Mosher, "Asymmetric Organic Reactions", 2nd Ed., American Chemical Society, Washington, D.C. (1976), which is incorporated herein by reference. Moreover, the reaction conditions are sufficiently mild that even complicated amino acids can be safely converted to the corresponding phosphonate.

VI. Uses of Chiral Phosphonates—Preparation of Peptidyl Phosphonates

The chiral alpha-amino phosphonates prepared according to this invention have various uses as discussed above and in copending U.S. patent application Ser. No. 08/119,700 (Attorney Docket No. 11509-59-2), U.S. patent application Ser. No. 07/943,805, filed Sep. 11, 1992, and U.S. patent application Ser. No. 08/081,577, filed Jun. 21, 1993, which are both incorporated herein by reference for all purposes. These uses include syntheses of stereospecific peptides having one or more phosphonate linkages (i.e. peptidylphosphonic acid derivatives). Further, by using suitable solid phase synthesis strategies, one can produce an array of phosphonic acid derivatives and screen that array for compounds with biological activity. In some embodiments, peptides both with and without phosphonate linkages may be produced on the same array. The phosphonates can also be used to prepare transition state analogs for use as haptens in eliciting monoclonal antibodies and for inhibiting certain enzymes.

To prepare peptidylphosphonic acid derivatives, a two step process is employed at each location in a growing peptide where a phosphonate linkage is to be introduced. First, an alphaohydroxy acid (such as an analog of a genetically coded alpha-amino acid) is coupled to the N-terminus of a growing peptide. Alphahydroxy acids are readily prepared following from commercially available amino acids using published techniques or the procedure set forth in copending U.S. application 07/943,805, filed Sep. 11, 1992, and U.S. patent application Ser. No. (Attorney docket No. 11509-59-1), filed Jun. 21, 1993, which are incorporated herein by reference.

Coupling the alpha-hydroxy acid to the N-terminus of a peptide produces a con, pound having an amide linkage and a free hydroxyl group on the terminus. Next, a chiral monoester of an alpha-aminophosphonic acid (prepared according to this reaction) is coupled to the hydroxyl group with activating reagents dialkylazodicarboxylate and triarylphospine, preferably with at least one of the aryl groups having an electronegative group, and optionally an exogenous base. See, e.g., U.S. patent application Ser. No. 08/119,700 (Attorney Docket No. 11509-59-2), U.S. patent application Ser. No. 07/943,805, filed Sep. 11, 1992, and U.S. patent application Ser. No. 08/081,577, filed Jun. 21, 1993. This introduces a phosphonate linkage in place of an amide linkage and presents an amine group on the peptidylphosphonate terminus for further reaction as desired. In this manner, one or more phosphonate linkages can be inserted at desired locations in a growing peptide.

Thus, the present invention provides a variety of methods for making, using, and screening chiral phosphonates and phosphonic acids. The above description and the following examples are intended to be illustrative and not restrictive. Many embodiments of the invention not explicitly set forth herein will be apparent to those of skill in the art upon reviewing this description of the invention. The disclosures of all articles and references, including patents and patent applications, in their entirety are incorporated herein by reference. The scope of the invention should be determined not with reference to the above description, but instead with reference to the appended claims, along with the full scope of equivalents to which such claims are entitled.

The following examples are provided to aid one of skill in the art in understanding the invention. Isolation and purification of the compounds and intermediates described in the examples can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures are in the examples below. Other equivalent separation or isolation procedures can, of course, also be used. These examples are for illustrative purposes only and are not to be construed as limiting this invention in any manner.

EXAMPLES

EXAMPLE 1

Preparation of Compounds of Formula III

To a solution of a compound of Formula I (1.0 retool) in dichloromethane (2–10 mL) cooled in an ice bath is added an alkyl or aryl peroxyacid, such as 3-chloroperoxybenzoic acid or peroxybenzoic acid, (1.1 retool) and then dicyclohexylcarbodiimide (1.1 mmol) with stirring. After evolution of carbon dioxide has ceased at 0° C. or room temperature, the mixture is filtered and chromatographed on a silica gel column.

EXAMPLE 2

Preparation of Compounds of Formula IV where X is —OH

A mixture of an ester of Formula III (1.69 mmol) in diethyl ether and 20% aqueous sodium hydroxide (10 mL) is refluxed with vigorous stirring for 24 hours. The aqueous layer is washed with ether and acidified with concentrated hydrochloric acid. The aqueous layer is washed with ethyl acetate. The organic layers are combined and concentrated under reduced pressure to yield the crude alcohol, which can be purified by column chromatography on silica gel.

EXAMPLE 3

Preparation of Compounds of Formula IV where X is —OTs

A solution of a compound of Formula IV where X is —OH (30 mmol), triethylamine (210 retool), and p-toluenesulfonyl chloride (210 mmol) in dichloromethane (100 mL) is stirred at 0° C for 30 minutes and then warmed to room temperature and stirred for an hour. The mixture is quenched with cold water and extracted with hexane's, dried over sodium sulfate, and concentrated under reduced pressure. The tosylate is typically used immediately without further purification.

EXAMPLE 4

Preparation of Compounds of Formula VI where X is —I

To a solution of a compound of Formula III in an aprotic solvent, such as carbon tetrachloride, is added iodotrimethylsilane (2.5 eq). The reaction mixture is stirred at 25°–80° C until complete and then filtered. The product can be purified by column chromatography on silica gel.

EXAMPLE 5

Preparation of Compounds of Formula VI where X is —OTs

To a solution of p-toluenesulfonic acid monohydrate (59 mml) in water (5 mL) is added a solution of zinc chloride (4.0 g) in water (2 mL). The white precipitate is filtered off, dried in vacuo at room temperature for one hour and stored in a stoppered flask.

To a solution of a compound of Formula IV where X is —OH (0.1 mmol) in benzene (2 mL) at room temperature is added triphenylphosphine (0.5 mmol) and zinc tosylate (prepared as described above, 0.06 retool). To the resulting suspension is added dropwise diethylazodicarboxylate (0.5 retool). The resulting clear solution is stirred at room temperature for 2 hours and then concentrated in vacuo. The product, a compound of Formula VI where X is —OTs can be purified by column chromatography.

EXAMPLE 6

Preparation of Compounds of Formula VI where X is —I

A solution of a compound of Formula IV where X is -p-toluenesulfonate (49.0 mmol) and sodium iodide (98.0 mmol) in acetonitrile (250 mL) is refluxed for 24 hours. The solution is cooled and concentrated under reduced pressure. The residue is diluted with ethyl acetate (500 mL), washed with water (300 mL) and concentrated in vacuo. The crude product is purified by column chromatography on silica gel.

EXAMPLE 7

Preparation of Compounds of Formula VI where X is —Br

By following the procedure set forth in Example 6 above and substituting sodium bromide for sodium iodide, compounds of Formula VI having bromide as the leaving group can be prepared.

EXAMPLE 8

Preparation of Compounds of Formula IV where X is —Br or —I

By following the procedures set forth in Example 6 and 7 above and substituting a compound of Formula VI where X is -p-toluenesulfonate for a compound of Formula IV, compounds of Formula IV where X is —Br or —I can be prepared.

EXAMPLE 9

Preparation of Compounds of Formula VI where X is —I

A mixture of a compound of Formula IV where X is —OH (2.5 mmol), finely ground triphenylphosphine (3.85 mmol), imidazole(7.72 mmol), and iodine (3.60 mmol) in toluene (50 mL) is vigorously stirred at 70° C. for 2.5 hours and then cooled. The mixture is diluted with water and extracted with toluene and concentrated in vacuo to yield a compound of Formula VI where X is —I.

EXAMPLE 10

Preparation of Compounds of Formulas V and VII

A solution of a compound of Formula IV or VI where X is —I, —Br, or —OTs (25.0 mmol) and a trialkylphosphite, preferably trimethylphosphite, in a polar aprotic solvent, such as methylene chloride, under an inert atmosphere is heated at reflux with stirring until the reaction is complete. The product, a compound of Formula V or VII may be isolated and purified by conventional means.

Although the foregoing invention has been described in some detail for purposes of clarity of understanding, it will be apparent that certain changes and modifications may be practiced within the scope of the appended claims.

What is claimed is:

1. A method of preparing a compound of Formula V:

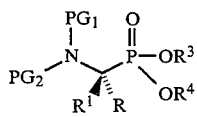

in which $PG_1$ and $PG_2$ are protecting groups, R and $R^1$ are independently selected from the group consisting of hydrogen, alkyl, aryl, substituted alkyl, substituted aryl, heteroaryl, alkylaryl, and aminoalkyl, provided that R is not the same as $R^1$ and provided that either R or $R^1$ is hydrogen, and R3 and $R^4$ are independently lower alkyl or aryl, the method comprising the steps of:

a) treating a compound of Formula I:

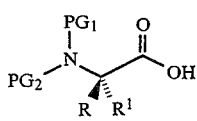

in which $PG_1$, $PG_2$, R, and $R^1$ are defined as above, with a peroxyacid having the structure $R^2(CO)OOH$, in which $R^2$ is alkyl or aryl, to yield an ester of Formula III:

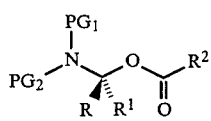

in which $PG_1$, $PG_2$, R, $R^1$, and $R^2$ are defined as above;

b) stereospecifically replacing the $R^2COO-$ group from the ester of Formula III with a leaving group X with retention of configuration, wherein the leaving group X is a halide or a sulfonate, to yield a compound of Formula IV

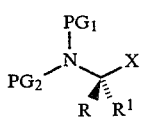

in which $PG_1$, $PG_2$, R, $R^1$, and X are defined as above; and c) treating the compound of Formula IV

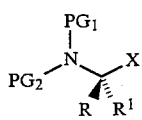

in which $PG_1$, $PG_2$, R, $R^1$, and X are defined as above, with a phosphite having the structure $P(OR^3)(OR^4)(OR^5)$, in which $R^3$, $R^4$, and $R^5$ are independently lower alkyl or aryl, to yield a compound of Formula V.

2. The method of claim 1 wherein the step of replacing the $R^2COO-$ group from the ester of Formula III with a leaving group comprises the step of treating the ester with $(CH_3)_3SiX$, where X is bromide or iodide, to produce a compound of Formula IV where X is bromide or iodide.

3. The method of claim I wherein the step of replacing the $R^2COO-$ group from the ester of Formula III with a leaving group comprises the steps of:

a) hydrolyzing the $R^2COO-$ group to produce a compound of Formula IV

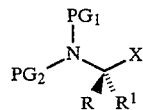

in which $PG_1$, $PG_2$, R, and $R^1$ are defined as above and X is $-OH$;

b) stereospecifically converting the compound of Formula IV in which $PG_1$, $PG_2$, R, and $R^1$ are defined as above and X is $-OH$, with retention of configuration, to yield a compound of Formula IV

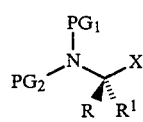

in which $PG_1$, $PG_2$, R, and $R^1$ are defined as above and X is a halide or a sulfonate.

4. The method of claim 1 wherein X is selected from the group consisting of bromide, iodide, p-toluenesulfonate, p-bromobenzenesulfonate, p-nitrobenzenesulfonate, methanesulfonate, trifluorome thanesulfonate, nonafluorobutanesulfonate, and 2,2,2-trifluoroethanesulfonate.

5. The method of claim 4 wherein X is p-toluenesulfonate.

6. The method of claim 1 wherein the peracid is selected from the group consisting of peroxybenzoic acid and 3-chloroperoxybenzoic acid.

7. The method of claim 6 wherein the peracid is 3-chloroperoxybenzoic acid.

8. The method of claim 1, further comprising the steps of:

a) hydrolyzing the compound of Formula V

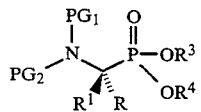

in which $PG_1$ and $PG_2$ are protecting groups, R and $R^1$ are independently selected from the group consisting of hydrogen, alkyl, aryl, substituted alkyl, substituted aryl, heteroaryl, alkylaryl, and aminoalkyl, provided that R is not the same as $R^1$ and provided that either R or $R^1$ is hydrogen, and $R^3$ and $R^4$ are independently lower alkyl or aryl, to produce a compound of Formula V

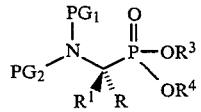

in which $PG_1$, $PG_2$, R, and $R^1$ are defined as above, and either $R^3$ or $R^4$ is hydrogen with the other being defined as above, and b) coupling the compound of Formula V

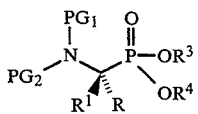

in which PG$_1$, PG$_2$, R, R$^1$, R$^3$, and R$^4$ are defined as above, with a hydroxyl group of a hydroxyl substituted amino acid to yield a peptidylphosphonate.

9. A method of preparing a compound of Formula VII:

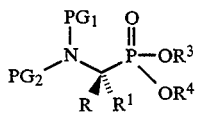

in which PG$_1$ and PG$_2$ are protecting groups, R and R$^1$ are independently selected from the group consisting of hydrogen, alkyl, aryl, substituted alkyl, substituted aryl, heteroaryl, alkylaryl, and aminoalkyl, provided that R is not the same as R$^1$ and provided that either R or R$^1$ is hydrogen, and R$^3$ and R$^4$ are independently lower alkyl or aryl, the method comprising the steps of:
a) treating a compound of Formula I:

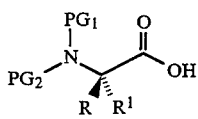

in which PG$_1$, PG$_2$, R, and R$^1$ are defined as above, with a peracid having the structure R$^2$(CO)OOH, in which R$^2$ is alkyl or aryl, to yield an ester of Formula III:

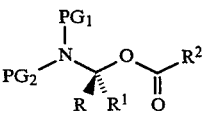

in which PG$_1$, PG$_2$, R, R$^1$, and R$^2$ are defined as above;
b) stereospecifically replacing the R$^2$COO— group from the ester of Formula III with a leaving group X with inversion of configuration, wherein the leaving group X is a halide or a sulfonate, to yield a compound of Formula VI

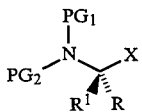

in which PG$_1$, PG$_2$, R, R$^1$, and X are defined as above; and
c) treating the compound of Formula VI

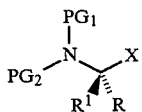

in which PG$_1$, PG$_2$, R, R$^1$, and X are defined as above, with a phosphite having the structure P(OR$^3$)(OR$^4$)(OR$^5$), in which R$^3$, R$^4$, R$^5$ are independently lower alkyl or aryl, to yield a compound of Formula VII.

10. The method of claim 9 wherein the step of replacing the R$^2$COO— group from the ester of Formula III with a leaving group comprises the step of treating the ester with (CH$_3$)$_3$SiX, where X is bromide or iodide, to produce a compound of Formula IV where X is bromide or iodide.

11. The method of claim 9 wherein the step of replacing the R$^2$COO— group from the ester of Formula III with a leaving group comprises the steps of:
a) hydrolyzing the R$^2$COO— group to produce a compound of Formula IV

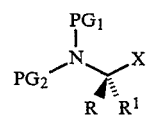

in which PG$_1$, PG$_2$, R, and R$^1$ are defined as above and X is —OH;
b) stereospecifically converting the compound of Formula IV in which PG$_1$, PG$_2$, R, and R$^1$ are defined as above and X is —OH, with inversion of configuration, to a compound of Formula VI

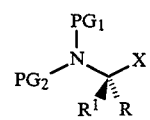

in which PG$_1$, PG$_2$, R, and R$^1$ are defined as above and X is a halide or a sulfonate.

12. The method of claim 9 wherein X is selected from the group consisting of bromide, iodide, p-toluenesulfonate, p-bromobenzenesulfonate, p-nitrobenzenesulfonate, methanesulfonate, trifluoromethanesulfonate, nonafluorobutanesulfonate, and 2,2,2-trifluoroethanesulfonate.

13. The method of claim 12 wherein X is p-toluenesulfonate.

14. The method of claim 9 wherein the peracid is selected from the group consisting of peroxybenzoic acid and 3-chloroperoxybenzoic acid.

15. The method of claim 13 wherein the peracid is 3-chloroperoxybenzoic acid.

16. The method of claim 9, further comprising the steps of:
a) hydrolyzing the compound of Formula VII

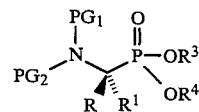

in which PG$_1$ and PG$_2$ are protecting groups, R and R$^1$ are independently selected from tile group consisting of hydrogen, alkyl, aryl, substituted alkyl, substituted aryl, heteroaryl, alkylaryl, and aminoalkyl, provided that R is not the same as R$^1$ and provided that either R or R$^1$ is hydrogen, and R$^3$ and R$^4$ are independently lower alkyl or aryl, to produce a con, pound of Formula VII

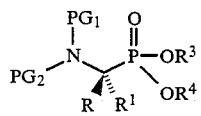
in which PG$_1$, PG$_2$, R, and R$^1$ are defined as above, and either R$^3$ or R$^4$ is hydrogen with the other being defined as above, and
b) coupling the compound of Formula VII
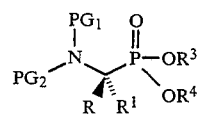
in which PG$_1$, PG$_2$, R, R$^1$, R$^3$, and R$^4$ are defined as above, with a hydroxyl group of a hydroxyl substituted amino acid to yield a peptidylphosphonate.
* * * * *